(12) United States Patent
Tsuzuki (10) Patent No.: US 7,449,343 B2
(45) Date of Patent: Nov. 11, 2008

(54) METHOD FOR MEASURING SURFACE PLASMON RESONANCE

(75) Inventor: Hirohiko Tsuzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 431 days.

(21) Appl. No.: 11/218,656

(22) Filed: Sep. 6, 2005

(65) Prior Publication Data

US 2006/0270061 A1    Nov. 30, 2006

(30) Foreign Application Priority Data

Sep. 7, 2004  (JP) ............................. 2004-259665
Sep. 29, 2004  (JP) ............................. 2004-284441

(51) Int. Cl.
  *G01N 33/558*  (2006.01)
  *G01N 33/553*  (2006.01)

(52) U.S. Cl. ..................... 436/514; 385/12; 385/129; 385/130; 422/58; 422/82.05; 422/82.11; 435/287.2; 435/288.7; 436/164; 436/525; 436/805

(58) Field of Classification Search .................... 385/12, 385/129, 130; 422/58, 82.05, 82.11; 435/287.2, 435/288.7; 436/164, 514, 525, 805
See application file for complete search history.

(56) References Cited

U.S. PATENT DOCUMENTS

| 5,629,213 | A | | 5/1997 | Kornguth et al. |
| 5,965,456 | A | * | 10/1999 | Malmqvist et al. .......... 436/514 |
| 6,330,062 | B1 | | 12/2001 | Corn et al. |
| 6,480,282 | B1 | | 11/2002 | Chinowsky et al. |
| 7,037,727 | B1 | * | 5/2006 | Miura et al. ................ 436/518 |
| 7,267,797 | B1 | * | 9/2007 | Craighead et al. ........ 422/82.05 |
| 2002/0177161 | A1 | | 11/2002 | Latov et al. |
| 2005/0146723 | A1 | | 7/2005 | Kuruma |
| 2006/0209305 | A1 | | 9/2006 | Kuruma |
| 2008/0037023 | A1 | | 2/2008 | Kuruma |

FOREIGN PATENT DOCUMENTS

| EP | 1 243 916 A2 | 3/2002 |
| JP | 2002-148188 A | 5/2002 |
| JP | 2005-164371 A | 6/2005 |
| JP | 2005-164372 A | 6/2005 |
| WO | WO 99/61896 A | 12/1999 |

OTHER PUBLICATIONS

Bothner, et al., "Defining the Molecular Basis of Arf and Hdm2 Interactions", Journal of Molecular Biology, London, GB, 2001, vol. 314, No. 2, pp. 263-277.

* cited by examiner

*Primary Examiner*—Christopher L Chin
(74) *Attorney, Agent, or Firm*—Sughrue Mion, PLLC (57) ABSTRACT

It is an object of the present invention to provide a measurement method which can suppress noise when a specific binding reaction between a physiologically active substance and a test substance is measured using a surface plasmon resonance measurement device. The present invention provides a method for measuring a change in surface plasmon resonance which comprises: using a surface plasmon resonance measurement device comprising a metal film, a light source for generating a light beam, an optical system for allowing the above-described light beam to enter the interface of the metal film so that total reflection conditions can be obtained at the interface thereof and so that various incidence angles can be included, a flow channel system comprising a cell formed on the above-described metal film, and a light-detecting means for detecting the state of surface plasmon resonance by measuring the intensity of the light beam totally reflected at the above interface, and exchanging the liquid contained in the above flow channel system with another liquid, wherein the liquid in the above-described flow channel system is exchanged with another liquid obtained by eliminating insoluble matters from a measurement solvent, and the change in surface plasmon resonance is then measured in a state where the flow of the liquid has been stopped.

17 Claims, 3 Drawing Sheets

METHOD FOR MEASURING SURFACE PLASMON RESONANCE

TECHNICAL FIELD

The present invention relates to a method for measuring surface plasmon resonance, and a method for detecting or measuring a substance interacting with a physiologically active substance using the above method.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The QCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences.

In all of the above-described techniques, the surface where a physiologically active substance is immobilized is important. Surface plasmon resonance (SPR), which is most commonly used in this technical field, will be described below as an example.

The surface plasmon resonance method, which enables the measurement of the change in the refractive index on the surface of gold at high sensitivity, is effective for searching a molecule binding to a protein by immobilizing the protein on the gold surface, or for analyzing the binding rate. At the same time, the surface plasmon resonance method is a method for measuring only the change in the refractive index on the gold surface, and thus signals are generated even from insoluble matters (contaminants) contained in a measurement solvent having a refractive index that is different from that of a sample solution. In particular, when contaminants of a large size, such as dusts, exist in a measurement solution, these contaminants cause large noise due to their large volume.

In order to solve this problem, it is conventionally proposed that a sample solution is previously filtrated (Japanese Patent Laid-Open (Kokai) No. 2001-148188). Japanese Patent Laid-Open (Kokai) No. 2001-148188 describes that analysis is carried out in a state where the solution continuously flows. However, such analysis has been problematic in that if the fraction size of a filter used in filtration is small, the filter is easily clogged, and a sufficient amount of solution cannot thereby be collected. In addition, such analysis has been also problematic in that if the fraction size of such a filter is large, contaminants cannot be eliminated to such an extent that it is sufficient for reducing noise. Moreover, although a sufficient amount of the filtrated solution can be obtained by increasing the area of a filter with respect to the amount of a sample solution to be filtrated, the decrease in molecules to be analyzed contained in a sample solution becomes not negligible in this case.

A commonly used measurement chip comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules. Examples of the surface plasmon resonance measurement device for carrying out the analysis as mentioned above include that of Japanese Patent Laid-Open (Kokai) No. 2001-330560.

When a specific binding reaction between a physiologically active substance and a test substance is measured, the binding reaction is generally measured by: connecting in series a reference cell, to which a physiologically active substance interacting with a test substance does not bind, with a detection cell, to which a physiologically active substance interacting with a test substance binds; placing the connected cells in a flow channel system; and feeding a liquid through the reference cell and the detection cell, so as to carry out the measurement of the binding reaction. During the measurement, the liquid contained in the above flow channel system is exchanged from a reference liquid containing no test substance to be measured to a sample liquid containing a test substance to be measured, so as to cause the binding reaction between the physiologically active substance and the test substance to be initiated, and to measure a change in signals due to a lapse of time. However, this measurement method is problematic in terms of the noise width of the change in signals during measurement. Thus, it has been difficult to obtain binding detection data with high reliability.

DISCLOSURE OF THE INVENTION

It is an object of the present invention to solve the aforementioned problems of the prior art techniques. In other words, it is an object of the present invention to provide a measurement method which can suppress noise when a specific binding reaction between a physiologically active substance and a test substance is measured using a surface plasmon resonance measurement device. Further, it is another object of the present invention to reduce the amount of a sample liquid necessary for measurement, when a specific binding reaction between a physiologically active substance and a test substance is measured using a surface plasmon resonance measurement device, thereby reducing noise caused by the liquid supplied during the measurement time.

As a result of intensive studies directed towards achieving the aforementioned object, the present inventors have found that when the change in surface plasmon resonance is measured using a surface plasmon resonance measurement device, by exchanging the liquid in a flow channel system with another liquid, the liquid in the above-described flow channel system is exchanged with a liquid obtained by eliminating insoluble matters from a measurement solvent, and the change in surface plasmon resonance is then measured in a state where the flow of the liquid has been stopped, thereby achieving the aforementioned object. Further, the present inventors have found that when the change in surface plasmon resonance is measured using a surface plasmon resonance measurement device, by exchanging the liquid in a flow channel system with another liquid, a sample liquid containing a test substance to be measured is intermittently supplied, and the change in surface plasmon resonance is then measured and extracted in a state where the flow of the liquid has been stopped, so as to achieve the aforementioned object. The present invention has been completed based on these findings.

That is to say, the present invention provides a method for measuring a change in surface plasmon resonance which comprises: using a surface plasmon resonance measurement device comprising a metal film, a light source for generating a light beam, an optical system for allowing the above-described light beam to enter the interface of the metal film so that total reflection conditions can be obtained at the interface thereof and so that various incidence angles can be included, a flow channel system comprising a cell formed on the above-described metal film, and a light-detecting means for detecting the state of surface plasmon resonance by measuring the intensity of the light beam totally reflected at the above interface, and exchanging the liquid contained in the above flow channel system with another liquid, wherein the liquid in the above-described flow channel system is exchanged with another liquid obtained by eliminating insoluble matters from a measurement solvent, and the change in surface plasmon resonance is then measured in a state where the flow of the liquid has been stopped.

Preferably, the liquid in the above-described flow channel system is exchanged from a reference liquid containing no test substances to be measured to a sample liquid containing a test substance to be measured which is obtained by eliminating insoluble matters from a measurement solvent, and thereafter, the change in surface plasmon resonance is measured in a state where the flow of the sample liquid has been stopped.

Preferably, the liquid which is obtained by eliminating insoluble matters from a measurement solvent is a filtrated liquid.

Preferably, the liquid which is obtained by eliminating insoluble matters from a measurement solvent is a liquid filtrated with a filter having a fraction size between 0.01 µm and 2 µm.

Preferably, the liquid which is obtained by eliminating insoluble matters from a measurement solvent is introduced into the flow channel system without allowing it to come into contact with outside air.

Preferably, the ratio (Ve/Vs) of the amount of a liquid exchanged for a single measurement (Ve ml) to the volume of the above-described cell (Vs ml) is between 1 and 100, and more preferably between 1 and 50.

Preferably, the time required for the exchange of the liquid in the above-described flow channel system is between 0.01 second and 100 seconds.

In another aspect, the present invention provides a method for detecting or measuring a substance interacting with a physiologically active substance, which uses at least a cell, onto the surface of which a physiologically active substance binds via a covalent bond, and which comprises steps of: allowing a sample liquid containing a test substance to be measured which is obtained by eliminating insoluble matters from a measurement solvent, to come into contact with the above-described cell; and measuring the change in surface plasmon resonance by the aforementioned method of the present invention.

In further another aspect, the present invention provides a method for measuring the change in surface plasmon resonance using a surface plasmon resonance measurement device comprising a flow channel system comprising a cell formed on a metal film and a light-detecting means for detecting the state of surface plasmon resonance by measuring the intensity of the light beam totally reflected at the face of the metal film, wherein the above-described method is characterized in that it comprises: intermittently supplying a sample liquid containing a test substance to be measured; and measuring and extracting the change in surface plasmon resonance in a state where the flow of the liquid has been stopped.

Preferably, there is used a surface plasmon resonance measurement device, which comprises: a dielectric block; a metal film formed on one side of the dielectric block; a light source for generating a light beam; an optical system for allowing the above-described light beam to enter the above-described dielectric block so that total reflection conditions can be obtained at the interface between the above-described dielectric block and the above-described metal film and so that various incidence angles can be included; a flow channel system comprising a cell formed on the above-described metal film; and a light-detecting means for detecting the state of surface plasmon resonance by measuring the intensity of the light beam totally reflected at the above-described interface.

Preferably, the ratio (Ve/Vs) of the amount of a sample liquid used for a single measurement (Ve ml) to the volume of the above-described cell (Vs ml) is between 1 and 100, and more preferably between 1 and 50.

Preferably, the time required for the supply of the liquid when the sample liquid is intermittently supplied is between 0.01 second and 10 seconds per a single operation.

Preferably, the time required for the stop of the liquid flow when the sample liquid is intermittently supplied is between 1 second and 20 seconds per a single operation.

In further another aspect, the present invention provides a method for detecting or measuring a substance interacting with a physiologically active substance, which uses at least a cell, onto the surface of which a physiologically active substance binds via a covalent bond, and which comprises a step of measuring the change in surface plasmon resonance by the aforementioned method of the present invention.

Preferably, the method of the present invention is a method for measuring the change in surface plasmon resonance by exchanging the liquid in a flow channel system with another liquid, wherein a sample liquid containing a test substance to be measured is intermittently supplied when a reference liquid containing no test substances to be measured, contained in the above flow channel system, is exchanged with the above sample liquid containing a test substance to be measured, and the change in surface plasmon resonance is then measured and extracted in a state where the flow of the liquid has been stopped.

BEST MODE FOR CARRYING OUT THE INVENTION

The embodiments of the present invention will be described below.

The first embodiment of the present invention relates to a method for measuring a change in surface plasmon resonance which comprises: using a surface plasmon resonance measurement device comprising a metal film, a light source for generating a light beam, an optical system for allowing the above-described light beam to enter the interface of the metal film so that total reflection conditions can be obtained at the interface thereof and so that various incidence angles can be included, a flow channel system comprising a cell formed on the above-described metal film, and a light-detecting means for detecting the state of surface plasmon resonance by measuring the intensity of the light beam totally reflected at the above interface, and exchanging the liquid contained in the above flow channel system with another liquid, wherein the above-described measurement method is characterized in that the liquid in the above-described flow channel system is exchanged with another liquid obtained by eliminating insoluble matters from a measurement solvent, and the change in surface plasmon resonance is then measured in a state where the flow of the liquid has been stopped.

One feature of the present invention resides in that the liquid in the above-described flow channel system is exchanged with a liquid which is obtained by eliminating insoluble matters (contaminants) from a measurement solvent. In the present invention, a means for eliminating insoluble matters from a measurement solvent is not particularly limited. For example, insoluble matters may be eliminated from a measurement solvent by filtration of the liquid, or an electric field or magnetic field may be applied to the liquid to eliminate such insoluble matters from the measurement solvent. Otherwise, the liquid may be subjected to centrifugation, so as to eliminate such insoluble matters from the measurement solvent. Preferably, insoluble matters can be eliminated from a measurement solvent by filtration of the liquid.

In the present invention, filtration can be carried out using a filter. The fraction size of a filter used in filtration is preferably between 0.01 μm and 2 μm, and more preferably between 0.05 μm and 1 μm.

The material of a filter used in filtration is not particularly limited. Preferred examples of a material used herein may include cellulose, acetylcellulose, nitrocellulose, nylon, polyvinylidene fluoride, Teflon, polyethylene, polypropylene, polyethylene terephthalate, acryl, polycarbonate, glass, and stainless. The form of a filter used in filtration is not particularly limited. Examples may include a membrane-type microfilter, nonwoven fabric, finished fabric, a film on which holes with a desired aperture are made by electron beam or the like, and a tube filled with beads or the like.

The filter used in filtration in the present invention may be subjected to surface treatment, so as to prevent adsorption of molecules to be analyzed thereon. Moreover, in order to specifically eliminate insoluble matters from a measurement solvent, products selectively binding to insoluble matters in a measurement solvent may be immobilized thereto.

Filtration of a sample liquid is carried out before the measurement of surface plasmon resonance in the present invention. After completion of the filtration, the filtrated liquid is preferably not allowed to come into contact with outside air, and more preferably, a filter is located at the midpoint of a flow channel for supplying a sample to a measurement unit.

In the present invention, the change in surface plasmon resonance is measured in a state where the flow of the liquid has been stopped. By such measurement, the noise width of the change in signals of a reference cell during the measurement time and the baseline fluctuation can be suppressed, and binding detection data with high reliability can thereby be obtained for the first time. The time required for the stop of the flow of the liquid is not particularly limited. For example, it is between 1 second and 30 minutes, preferably between 10 seconds and 20 minutes, and more preferably between 1 minute and 20 minutes.

Preferably in the present invention, the liquid in the above-described flow channel system is exchanged from a reference liquid containing no test substances to be measured to a sample liquid containing a test substance to be measured which is obtained by eliminating insoluble matters from a measurement solvent, and thereafter, the change in surface plasmon resonance can be measured in a state where the flow of the sample liquid has been stopped.

The second embodiment of the present invention relates to a method for measuring the change in surface plasmon resonance using a surface plasmon resonance measurement device comprising a flow channel system comprising a cell formed on a metal film and a light-detecting means for detecting the state of surface plasmon resonance by measuring the intensity of the light beam totally reflected at the face of the metal film, wherein the above-described method is characterized in that it comprises: intermittently supplying a sample liquid containing a test substance to be measured; and measuring and extracting the change in surface plasmon resonance in a state where the flow of the liquid has been stopped.

In the present invention, a sample liquid containing a test substance to be measured is intermittently supplied, and the change in surface plasmon resonance is then measured and extracted in a state where the flow of the solution has been stopped, so as to reduce the noise width of the change in signals during the measurement time. Thus, binding detection data with high reliability can be obtained.

The time required for the supply of the liquid when the sample liquid is intermittently supplied is preferably between 0.01 second and 10 seconds per a single operation, and more preferably between 0.01 second and 5 seconds per a single operation.

The time required for the stop of the solution flow when the sample liquid is intermittently supplied is preferably between 1 second and 20 seconds per a single operation, and more preferably between 1 second and 10 seconds per a single operation.

In the present invention, the change in surface plasmon resonance is measured and extracted in a state of the flow of the solution has been stopped. The term "extraction" is used herein to mean the extraction of data regarding the change in surface plasmon resonance. Thus, all the change in surface plasmon resonance in a state where the flow of the solution has been stopped may be extracted, or only a portion thereof may be extracted. That is to say, it may also be possible to extract the change in surface plasmon resonance in a part of time during the time at which the flow of the solution has been stopped.

Preferably in the first and second embodiments of the present invention as mentioned above, a reference cell, to which a substance interacting with a test substance does not bind, is connected in series with a detection cell, to which such a substance interacting with a test substance binds; the thus connected cells are placed in a flow channel system; and a liquid is then fed through the reference cell and the detection cell, and then, the change in surface plasmon resonance can be measured.

In addition, in the first and second embodiments of the present invention as mentioned above, the ratio (Ve/Vs) of the amount of a liquid exchanged (Ve ml) in a single measurement to the volume (Vs ml) of a cell used in measurement (when the aforementioned reference cell and detection cell are used, the total volume of these cells) is preferably between 1 and 100. Ve/Vs is more preferably between 1 and 50, and particularly preferably between 1 and 20. The volume (Vs ml) of a cell used in measurement is not particularly limited. It is preferably between $1\times10^{-6}$ and 1.0 ml, and particularly preferably between $1\times10^{-5}$ and $1\times10^{-1}$ ml. The period of time necessary for exchanging the liquid is preferably between 0.01 second and 100 seconds, more preferably between 0.1 second and 10 seconds.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light. The surface plasmon resonance measurement device used in the present invention will be described below.

The surface plasmon resonance measurement device is a device for analyzing the properties of a substance to be measured using a phenomenon whereby a surface plasmon is excited with a lightwave. The surface plasmon resonance measurement device used in the present invention comprises a dielectric block, a metal film formed on a face of the dielectric block, a light source for generating a light beam, an optical system for allowing the above light beam to enter the above dielectric block such that total reflection conditions can be obtained at the interface between the above dielectric block and the above metal film and that components at various incident angles can be contained, and a light-detecting means for detecting the state of surface plasmon resonance by measuring the intensity of the light beam totally reflected at the above interface.

Moreover, as stated above, the above dielectric block is formed as one block comprising the entity of the entrance face and exit face of the above light beam and a face on which the above metal film is formed, and the above metal film is integrated with this dielectric block.

In the present invention, more specifically, a surface plasmon resonance measurement device shown in FIGS. 1 to 32 of Japanese Patent Laid-Open No. 2001-330560, and a surface plasmon resonance device shown in FIGS. 1 to 15 of Japanese Patent Laid-Open No. 2002-296177, can be preferably used. All of the contents as disclosed in Japanese Patent Laid-Open Nos. 2001-330560 and 2002-296177 cited in the present specification are incorporated herein by reference as a part of the disclosure of this specification.

For example, the surface plasmon resonance measurement device described in Japanese Patent Laid-Open No. 2001-330560 is characterized in that it comprises: a dielectric block; a thin metal film formed on a face of the dielectric block; multiple measurement units comprising a sample-retaining mechanism for retaining a sample on the surface of the thin film; a supporting medium for supporting the multiple measurement units; a light source for generating a light beam; an optical system for allowing the above light beam to enter the dielectric block at various angles so that total reflection conditions can be obtained at the interface between the dielectric block and the metal film; a light-detecting means for measuring the intensity of the light beam totally reflected at the above interface and detecting the state of attenuated total reflection caused by surface plasmon resonance; and a driving means for making the above supporting medium, the above optical system and the above light-detecting means move relative to one another, and successively placing each of the above multiple measurement units in a certain position appropriate to the above optical system and the above light-detecting means, so that the above total reflection conditions and various incident angles can be obtained with respect to each dielectric block of the above multiple measurement units.

It is to be noted that in the above measurement device, the above optical system and light-detecting means are kept in a resting state and the above driving means makes the above supporting medium move.

In such a case, the above supporting medium is desirably a turntable for supporting the above multiple measurement units on a circle centered on a rotation axis, and the above driving means is desirably a means for intermittently rotating this turntable. In this case, a medium for supporting the above multiple measurement units that are linearly arranged in a line may be used as the above supporting medium, and a means that makes such a supporting medium move linearly in an intermittent fashion in the direction in which the above multiple measurement units are arranged may be applied as the above driving means.

Otherwise, on the contrary, it may also be possible that the above supporting medium be retained in a resting state and that the above driving means makes the above optical system and light-detecting means move.

In such a case, the above supporting medium is desirably a medium for supporting the above multiple measurement units on a circle, and the above driving means is desirably a means for intermittently rotating the above optical system and light-detecting means along the multiple measurement units supported by the above supporting medium. In this case, a medium for supporting the above multiple measurement units that are linearly arranged in a line may be used as the above supporting medium, and a means that makes the above optical system and light-detecting means move linearly in an intermittent fashion along the multiple measurement units supported by the above supporting medium may be applied as the above driving means.

Otherwise, when the above driving means has a rolling bearing that supports a rotation axis, the driving means is desirably configured such that after the rotation axis has been rotated to a certain direction and a series of measurements for the above multiple measurement units has been terminated, the above rotation axis is equivalently rotated to the opposite direction, and then it is rotated again to the same above direction for the next series of measurements.

In addition, the above-described measurement device is desirably configured such that the above multiple measurement units are connected in a line with a connecting member so as to constitute a unit connected body and that the above supporting medium supports the unit connected body.

Moreover, in the above-described measurement device, it is desirable to establish a means for automatically feeding a given sample to each sample-retaining mechanism of the multiple measurement units supported by the above supporting medium.

Furthermore, in the above-described measurement device, it is desirable that the dielectric block of the above measurement unit be immobilized to the above supporting medium, that a thin film layer and a sample-retaining mechanism of the measurement unit be unified so as to constitute a measurement chip, and that the measurement chip be formed such that it is exchangeable with respect to the above dielectric block.

When such a measurement chip is applied, it is desirable to establish a cassette for accommodating a multiple number of the measurement chips and a chip-supplying means for successively taking a measurement chip out of the cassette and supplying it in a state in which it is connected to the above dielectric block.

Otherwise, it may also be possible to unify the dielectric block of the measurement unit, the thin film layer and the sample-retaining mechanism, so as to constitute a measurement chip, and it may also be possible for this measurement chip to be formed such that it is exchangeable with respect to the above supporting medium.

When a measurement chip has such a structure, it is desirable to establish a cassette for accommodating a multiple number of measurement chips and a chip-supplying means for successively taking a measurement chip out of the cassette and supplying it in a state in which it is supported by the supporting medium.

The above optical system is desirably configured such that it makes a light beam enter the dielectric block in a state of convergent light or divergent light. Moreover, the above light-detecting means is desirably configured such that it detects the position of a dark line generated due to attenuated total reflection, which exists in the totally reflected light beam.

Furthermore, the above optical system is desirably configured such that it makes a light beam enter the above interface in a defocused state. In this case, the beam diameter of the light beam at the above interface in a direction wherein the above supporting medium moves is desirably ten times or greater the mechanical positioning precision of the above supporting medium.

Still further, the above-described measurement device is desirably configured such that the measurement unit is supported on the upper side of the above supporting medium, such that the above light source is placed so as to project the above light beam from a position above the above supporting medium to downwards, and such that the above optical system comprises a reflecting member for reflecting upwards the above light beam projected to downwards as described above and making it proceed towards the above interface.

Still further, the above-described measurement device is desirably configured such that the above measurement unit is supported on the upper side of the above supporting medium, such that the above optical system is constituted so as to make the above light beam enter the above interface from the downside thereof, and such that the above light-detecting means is placed in a position above the above supporting medium with a light-detecting plane thereof facing downwards, as well as comprising a reflecting member for reflecting upwards the totally reflected light beam at the above interface and making it proceed towards the above light-detecting means.

What is more, the above-described measurement device desirably comprises a temperature-controlling means for maintaining the temperature of the above measurement unit before and/or after being supported by the above supporting medium at a predetermined temperature.

Moreover, the above-described measurement device desirably comprises a means for stirring the sample stored in the sample-retaining mechanism of the measurement unit supported by the above supporting medium before detecting the state of attenuated total reflection as mentioned above.

Furthermore, in the above-described measurement device, it is desirable to establish in at least one of the multiple measurement units supported by the above supporting medium a standard solution-supplying means for supplying a standard solution having optical properties associated with the optical properties of the above sample, as well as a correcting means for correcting data regarding the above attenuated total reflection state of the sample based on the data regarding the above attenuated total reflection state of the above standard solution.

In such a case, if the sample is obtained by dissolving a test substance in a solvent, it is desirable that the above standard solution-supplying means be a means for supplying the above solvent as a standard solution.

Still further, the above measurement device desirably comprises: a mark for indicating individual recognition information; a reading means for reading the above mark from the measurement unit used in measurement; an inputting means for inputting sample information regarding the sample supplied to the measurement unit; a displaying means for displaying measurement results; and a controlling means connected to the above displaying means, inputting means and reading means, which stores the above individual recognition information and sample information of each measurement unit while associating them with each other, as well as making the above displaying means display the measurement results of the sample retained in a certain measurement unit while associating them with the above individual recognition information and sample information of each measurement unit.

When a substance interacting with a physiologically active substance is detected or measured using the above-described measurement device, a state of attenuated total reflection is detected in a sample contained in one of the above measurement units, and thereafter, the above supporting medium, optical system and light-detecting means are moved relative to one another, so that a state of attenuated total reflection is detected in a sample contained in another measurement unit. Thereafter, the above supporting medium, optical system and light-detecting means are again moved relative to one another, so that a state of attenuated total reflection is detected again the sample contained in the above one measurement unit, thereby completing the measurement.

The measurement chip used in the present invention is used for the surface plasmon resonance measurement device having a structure described herein, and comprises a dielectric block and a metal film formed on a face of the dielectric block, in which the dielectric block is formed as one block comprising the entirety of the entrance face and exit face of the light beam and a face on which the above metal film is formed, the above metal film is integrated with the above dielectric block.

A metal constituting the metal film is not particularly limited, as long as surface plasmon resonance is generated. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 0.1 nm and 500 nm, and particularly preferably between 1 nm and 200 nm. If the thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and having excellent workability are preferably used.

Preferably, the metal film has a functional group capable of immobilizing a physiologically active substance on the outermost surface of the substrate. The term "the outermost surface of the substrate" is used to mean "the surface, which is farthest from the substrate".

Examples of a preferred functional group may include —OH, —SH, —COOH, —NR$^1$R$^2$ (wherein each of R$^1$ and R$^2$ independently represents a hydrogen atom or lower alkyl group), —CHO, —NR$^3$NR$^1$R$^2$ (wherein each of R$^1$, R$^2$ and R$^3$ independently represents a hydrogen atom or lower alkyl group), —NCO, —NCS, an epoxy group, and a vinyl group. The number of carbon atoms contained in the lower alkyl group is not particularly limited herein. However, it is generally about C1 to C10, and preferably C1 to C6.

Examples of the method of introducing such a functional group include a method which involves applying a polymer containing a precursor of such a functional group on a metal surface or metal film, and then generating the functional group from the precursor located on the outermost surface by chemical treatment.

In the measurement chip obtained as mentioned above, a physiologically active substance is covalently bound thereto via the above functional group, so that the physiologically active substance can be immobilized on the metal film.

A physiologically active substance immobilized on the surface for the measurment chip of the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against 0 antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

When a physiologically active substance is a protein such as an antibody or enzyme, or nucleic acid, an amino group, thiol group or the like of the physiologically active substance is covalently bound to a functional group located on a metal surface, so that the physiologically active substance can be immobilized on the metal surface.

A measurement chip to which a physiologically active substance is immobilized as described above can be used to detect and/or measure a substance which interacts with the physiologically active substance.

Namely, the present invention provides a method for detecting or measuring a substance interacting with a physiologically active substance, which uses at least a a measurement chip (cell), onto the surface of which a physiologically active substance binds via a covalent bond, and which comprises steps of: allowing a sample liquid containing a test substance to be measured which is obtained by eliminating insoluble matters from a measurement solvent, to come into contact with the above-described cell; and measuring the change in surface plasmon resonance in a state where the flow of the liquid has been stopped.

Namely, the present invention provides a method for detecting or measuring a substance interacting with a physiologically active substance, which uses at least a a measurement chip (cell), onto the surface of which a physiologically active substance binds via a covalent bond, and which comprises steps of: intermittently supplying a sample liquid containing a test substance to be measured when a reference liquid containing no test substances to be measured, contained in the above flow channel system, is exchanged with the sample liquid containing a test substance to be measured, and then measuring and extracting the change in surface plasmon resonance in a state where the flow of the liquid has been stopped.

As a test substance, a sample containing a substance interacting with the aforementioned physiologically active substance can be used, for example.

The present invention is described in more detail by the following Examples, but the present invention is not limited by the Examples.

EXAMPLES

Example 1

The following experiment was conducted using SPRimager manufactured by GWC.

(1) Production of Dextran Measurement Chip

An optically polished glass plate (BSC7 manufactured by HOYA) with a thickness of 0.3 mm was coated with 50 nm of gold via evaporation. The thus obtained glass plate coated with a metal film was treated with a Model-208 UV-ozone cleaning system (TECHNOVISION INC.) for 30 minutes. Thereafter, a solution of 5.0 mM 11-hydroxy-1-undecanethiol in ethanol/water (80/20) was added to the glass plate, such that the solution was allowed to come into contact with the metal film, and the surface treatment was carried out at 25° C. for 18 hours. Thereafter, the resultant was washed with ethanol 5 times, then with an ethanol/water mixed solvent once, and then with water 5 times.

Subsequently, the surface coated with 11-hydroxy-1-undecanethiol was allowed to come into contact with 10%-by-weight epichlorohydrin solution (solvent: a mixed solution of 0.4 M sodium hydroxide and diethylene glycol dimethyl ether at a ratio of 1:1), and the reaction was then proceeded in a shaking incubator at 25° C. for 4 hours. Thereafter, the surface was washed with ethanol twice and then with water 5 times.

Subsequently, 4.5 ml of 1 M sodium hydroxide was added to 40.5 ml of a 25%-by-weight dextran (T500, Pharmacia) aqueous solution, and the obtained solution was then allowed to come into contact with the surface treated with epichlorohydrin. Thereafter, it was incubated in a shaking incubator at 25° C. for 20 hours. Thereafter, the surface was washed with water at 50° C. 10 times. Thereafter, a mixture obtained by dissolving 3.5 g of bromoacetic acid in 27 g of a 2 M sodium hydroxide solution was allowed to come into contact with the above-described surface treated with dextran, and it was then incubated in a shaking incubator at 28° C. for 16 hours. Thereafter, the surface was washed with water. The aforementioned procedure was repeated once.

(2) Production of Trypsin-immobilized Chip

The solution in the dextran measurement chip produced in (1) above was removed. Thereafter, the chip was immersed in a mixed solution of 200 mM EDC (N-ethyl-N'-(3-dimethylaminopropyl)carbodiimide hydrochloride) and 50 mM NHS (N-hydroxysuccinimide), and it was then left for 10 minutes. The mixed solution was removed, and the chip was then washed with water 3 times and then with buffer 1 (10 mM HEPES (N-2-hydroxyethylpiperazin-N'-2-ethanesulfonic acid), 150 mM NaCl, and 10 mM $CaCl_2$) 3 times.

Figure 1:
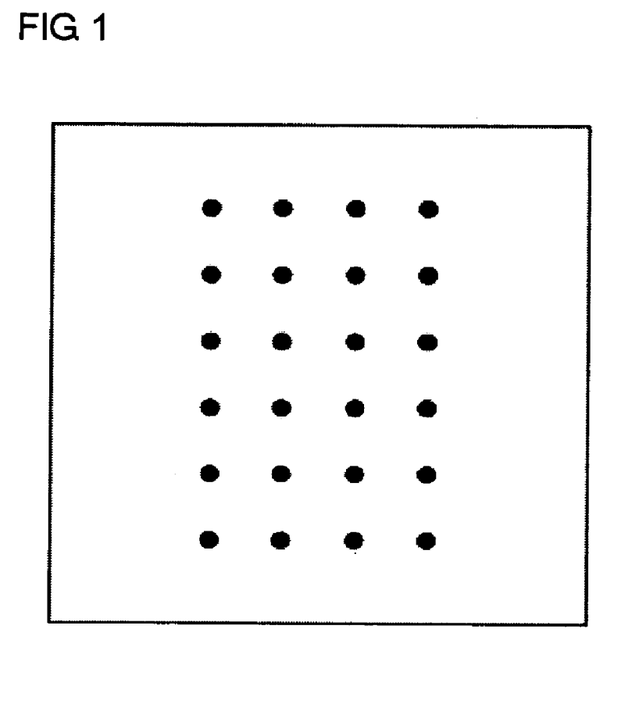
FIG. 1 shows a mark made from Teflon with holes.
Figure 2:
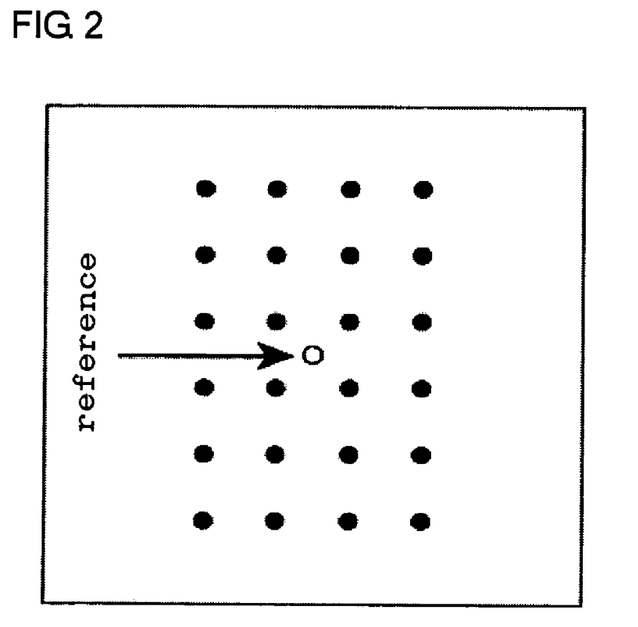
FIG. 2 shows a chip, on the black portions of which trypsin was immobilized.

Subsequently, a mask with a thickness of 100 μm made from Teflon, which had thereon holes shown as black portions in FIG. 1, was pressed against the chip, and a trypsin solution (trypsin was dissolved in buffer 1 to a concentration of 1 mg/ml) was placed in the holes. The mask and the chip were left for 30 minutes for immobilization of trypsin. A black portion in FIG. 1 has an inside diameter of 500 μm, and such a black portion is at a distance of 2 mm from another black portion adjacent thereto, as a center-to-center distance. The solution in the chip was replaced with 1 M ethanolamine solution, and it was then left for 10 minutes. The inside of the holes was washed 10 times with buffer 1. Thus, trypsin was immobilized in the black portions shown in FIG. 2.

The aforementioned trypsin-immobilized chip was immersed in 1 M ethanolamine solution for 10 minutes, and then washed 10 times with buffer 1, so as to produce a trypsin-immobilized chip.

(3) Evaluation of Ability to Bind to Anti-trypsin Antibody

The trypsin-immobilized chip produced in (2) above was placed in a surface plasmon resonance measurement device. A sucrose solution, the refractive index of which had previously been known, was supplied, so that a calibration curve regarding the output of the surface plasmon device to the refractive index was produced. Herein, the change in the refractive index around the metal surface linearly correlated with the adsorbed amount of a molecule to be analyzed (anti-trypsin antibody). The value which is obtained by calibrating the output from the surface plasmon device into the refractive index using this calibration curve is defined as a surface plasmon signal.

The inside of the flow channel system was filled with buffer 2 (10 mM HEPES, 150 mM NaCl). Using, as a reference, the signal of a reference portion shown in FIG. 2, on which trypsin had not been immobilized, the change in signals (R) in the center of the trypsin-immobilized portion was measured. Meanwhile, each of anti-trypsin antibody solutions (obtained by dissolving the above antibody in buffer 2, resulting in a concentration of 1 μg/ml) (samples 1 to 6 described below) was supplied into the flow channel system. Such supply of the above antibody solution was stopped, immediately after the solution was replaced with the above antibody solution. Subsequently, buffer 2 was supplied into the flow channel system. Such supply of buffer 2 was stopped, immediately after the value in the reference portion was returned to the value obtained before the supply of the anti-trypsin antibody solution. The signal in the center of each of 12 black circles shown in FIG. 2 was measured, and the obtained value was defined as the binding amount of the anti-trypsin antibody. The reproducibility of measurement was evaluated by the value obtained by dividing the standard deviation of the signals of these 12 circles by a mean value. The smaller the above value, the smaller the noise that can be obtained.

Sample 1: An anti-trypsin antibody solution, which was left in a laboratory at 25° C. for 8 hours without being capped.

Sample 2: A sample (immediately after filtration) obtained by filtration of the aforementioned sample 1 with a polyethylene terephthalate filter having a fraction size of 0.45 μm immediately before measurement.

Sample 3: A sample obtained by leaving the aforementioned sample 2 again in a laboratory at 25° C. for 1 hour without being capped.

Sample 4: A sample obtained by leaving the aforementioned sample 2 again in a laboratory at 25° C. for 1 hour with being capped.

Sample 5: When the aforementioned sample 1 was measured, a cellulose acetate microfilter having a fraction size of 0.22 μm was inserted into a portion just before the surface plasmon measurement unit for filtration, and immediately after the filtration, the sample was measured.

Sample 6: An anti-trypsin antibody solution was continuously supplied for 10 minutes under the same conditions as those for sample 5, and thereafter, buffer 2 was continuously supplied into the flow channel system.

The results of the aforementioned measurement are shown in Table 1 below. Good results were obtained in the case of the samples (samples 2 to 5) of the present invention.

TABLE 1

| Sample | Standard deviation/mean value | |
|---|---|---|
| 1 | 0.64 | Comparative example |
| 2 | 0.17 | The present invention |
| 3 | 0.32 | The present invention |
| 4 | 0.18 | The present invention |
| 5 | 0.02 | The present invention |
| 6 | Measurement was unsuccessful because of separation of a solution-supplying hose. | Comparative example |

Example 2

The following experiment was conducted using SPRimager manufactured by GWC.

(1) Production of Dextran Measurement Chip

An optically polished glass plate (BSC7 manufactured by HOYA) with a thickness of 0.3 mm was coated with 50 nm of gold via evaporation. The thus obtained glass plate coated with a metal film was treated with a Model-208 UV-ozone cleaning system (TECHNOVISION INC.) for 30 minutes. Thereafter, a solution of 5.0 mM 11-hydroxy-1-undecanethiol in ethanol/water (80/20) was added to the glass plate, such that the solution was allowed to come into contact with the metal film, and the surface treatment was carried out at 25° C. for 18 hours. Thereafter, the resultant was washed with ethanol 5 times, then with an ethanol/water mixed solvent once, and then with water 5 times.

Subsequently, the surface coated with 11-hydroxy-1-undecanethiol was allowed to come into contact with 10%-by-weight epichlorohydrin solution (solvent: a mixed solution of 0.4 M sodium hydroxide and diethylene glycol dimethyl ether at a ratio of 1:1), and the reaction was then proceeded in a shaking incubator at 25° C. for 4 hours. Thereafter, the surface was washed with ethanol twice and then with water 5 times.

Subsequently, 4.5 ml of 1 M sodium hydroxide was added to 40.5 ml of a 25%-by-weight dextran (T500, Pharmacia) aqueous solution, and the obtained solution was then allowed to come into contact with the surface treated with epichlorohydrin. Thereafter, it was incubated in a shaking incubator at 25° C. for 20 hours. Thereafter, the surface was washed with water at 50° C. 10 times. Thereafter, a mixture obtained by dissolving 3.5 g of bromoacetic acid in 27 g of a 2 M sodium hydroxide solution was allowed to come into contact with the above-described surface treated with dextran, and it was then incubated in a shaking incubator at 28° C. for 16 hours. Thereafter, the surface was washed with water. The aforementioned procedure was repeated once.

(2) Production of Protein A-immobilized Chip

The solution in the dextran measurement chip produced in (1) above was removed. Thereafter, the chip was immersed in a mixed solution of 200 mM EDC (N-ethyl-N'-(3-dimethylaminopropyl)carbodiimide hydrochloride) and 50 mM NHS (N-hydroxysuccinimide), and it was then left for 10 minutes. The mixed solution was removed, and the chip was then washed with water 3 times and then with buffer 1 (10 mM HEPES (N-2-hydroxyethylpiperazin-N'-2-ethanesulfonic acid), 150 mM NaCl, and 10 mM $CaCl_2$) 3 times.

Subsequently, a protein A solution (protein A was dissolved in buffer 1 to a concentration of 1 mg/ml) that was in the form of a droplet with a diameter of 2 mm was placed in the center of the chip, so that protein A was immobilized thereon partially. The inside of the chip was replaced with 1 M ethanolamine solution, and it was then left for 10 minutes. Thereafter, it was washed 10 times with buffer 1. Thus, protein A was partially immobilized on the chip. The trypsin-immobilized chip was immersed in 1 M ethanolamine solution for 10 minutes, and it was then washed 10 times with buffer 1, so as to produce a protein A-immobilized chip.

(3) Evaluation of Ability of IgG Binding

The thus obtained protein A-immobilized chip was placed in a surface plasmon resonance measurement device (SPRimager manufactured by GWC). A flow channel was produced with polydimethyl siloxane, and it was attached to the chip such that the height thereof became 100 μm. A Teflon tube with an inside diameter of 0.5 mm and an outside diameter of 1 mm was put in each of the solution-supplying side and solution-discharging side of the flow channel, and it was then sealed with polydimethyl siloxane, thereby enabling the supply of the solution.

A sucrose solution, the refractive index of which had previously been known, was supplied, so that a calibration curve regarding the output of the surface plasmon device to the refractive index was produced. Herein, the change in the refractive index around the metal surface linearly correlated with the adsorbed amount of a molecule to be analyzed (IgG). The value which is obtained by calibrating the output from the surface plasmon device into the refractive index using this calibration curve is defined as a surface plasmon signal.

Figure 3:
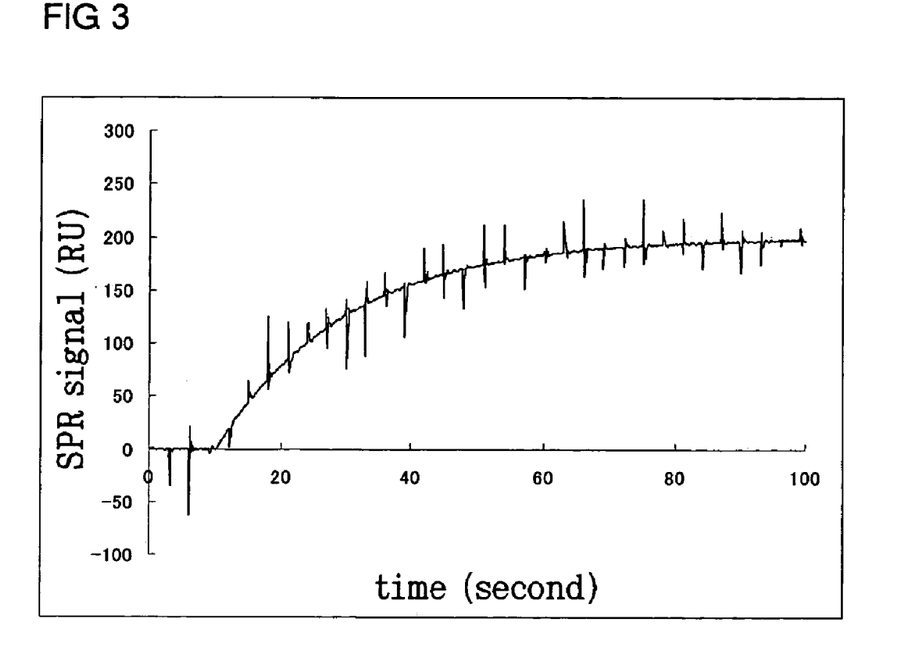
FIG. 3 shows a sensorgram which is obtained when the IgG solution was intermittently supplied into a flow channel system.
Figure 4:
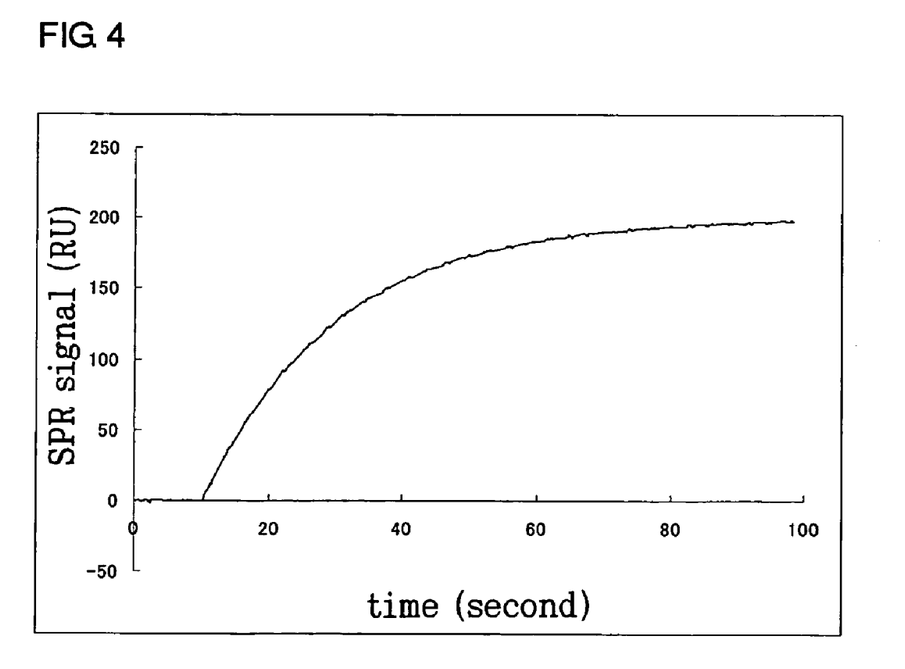
FIG. 4 shows only a time portion at which the solution had not been supplied (a time portion from 1 second to 2.5 seconds after the supply of the solution), which was extracted from the sensorgram shown in FIG. 1.
Figure 5:
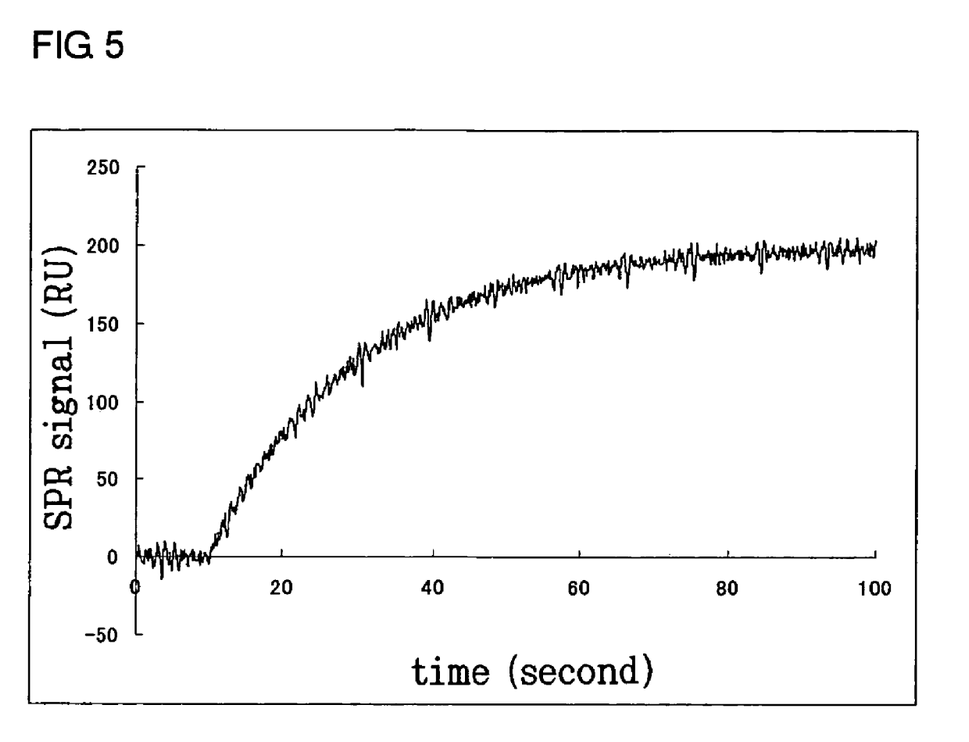
FIG. 5 shows a sensorgram obtained when the IgG solution was continuously supplied into a flow channel system at a linear velocity of 0.1 m/min.

The inside of the flow channel system was filled with buffer 2 (10 mM HEPES, 150 mM NaCl). Using, as a reference, a region that was at a distance of 200 μm or more from the protein A-immobilized portion, the change in signals (R) in the center of the protein A-immobilized portion was measured. Meanwhile, an IgG solution (obtained by dissolving the above IgG in buffer 2, resulting in a concentration of 10 μg/ml) was supplied for 0.1 second into the flow channel system at a rate causing a linear velocity of 3 m/min on the surface of the metal film. Thereafter, the supply of the solution was stopped for 3 seconds. At this time, Ve/Vs was 10. This operation was repeatedly carried out, so as to obtain the sensorgram shown in FIG. 3. FIG. 4 shows another sensorgram, which was obtained by extracting from the thus obtained sensorgram shown in FIG. 3, a time portion at which the solution has not been supplied, namely, a time portion from 1 second to 2.5 seconds after the supply of the solution. As a comparative example, FIG. 5 shows a sensorgram obtained when the solution was continuously supplied at a linear velocity of 0.1 m/min. When compared with the sensorgram shown in FIG. 4 obtained by the method of the present invention, the sensorgram shown in FIG. 5 has noise that is approximately 10 times higher than that of the sensorgram in FIG. 4.

EFFECTS OF THE INVENTION

According to the measurement method of the present invention, the amount of a sample liquid necessary for measurement can be reduced, and highly reliable measurement results with suppressed noise can be obtained.

The invention claimed is:

1. A method for measuring a change in surface plasmon resonance which comprises: using a surface plasmon resonance measurement device comprising a metal film, a light source for generating a light beam, an optical system for allowing the above-described light beam to enter the interface of the metal film so that total reflection conditions can be obtained at the interface thereof and so that various incidence angles can be included, a flow channel system comprising a cell formed on the above-described metal film, and a light-detecting means for detecting the state of surface plasmon resonance by measuring the intensity of the light beam totally reflected at the above interface, and exchanging a liquid contained in the above flow channel system with another liquid, wherein the liquid in the above-described flow channel system is exchanged with another liquid obtained by eliminating insoluble matters from a measurement solvent, and the change in surface plasmon resonance is then measured in a state where the flow of the liquid in the flow channel system has been stopped.

2. The measurement method of claim 1 wherein the liquid in the flow channel system is a reference liquid containing no test substances to be measured which is exchanged by a sample liquid containing a test substance to be measured which is obtained by eliminating insoluble matters from a measurement solvent, and thereafter, the change in surface plasmon resonance is measured in a state where the flow of the sample liquid has been stopped.

3. The measurement method of claim 1 wherein the liquid which is obtained by eliminating insoluble matters from a measurement solvent is a filtrated liquid.

4. The measurement method of claim 1 wherein the liquid which is obtained by eliminating insoluble matters from a measurement solvent is a liquid filtrated with a filter having a fraction size between 0.01 µm and 2 µm.

5. The measurement method of claim 1 wherein the liquid which is obtained by eliminating insoluble matters from a measurement solvent is introduced into the flow channel system without allowing it to come into contact with outside air.

6. The measurement method of claim 1 wherein the ratio (Ve/Vs) of the amount of a liquid exchanged for a single measurement (Ve ml) to the volume of the above-described cell (Vs ml) is between 1 and 100.

7. The measurement method of claim 6 wherein the ratio (Ve/Vs) is between 1 and 50.

8. The measurement method of claim 1 wherein the time required for the exchange of the liquid in the flow channel system is between 0.01 second and 100 seconds.

9. A method for detecting or measuring a substance interacting with a physiologically active substance, which uses at least a cell, onto the surface of which a physiologically active substance binds via a covalent bond, and which comprises steps of: allowing a sample liquid containing a test substance to be measured which is obtained by eliminating insoluble matters from a measurement solvent, to come into contact with the above-described cell; and measuring the change in surface plasmon resonance by the method of claim 1 to determine the presence of the substance interacting with the physiologically active substance.

10. A method for measuring the change in surface plasmon resonance using a surface plasmon resonance measurement device comprising a flow channel system comprising a cell formed on a metal film and a light-detecting means for detecting the state of surface plasmon resonance by measuring the intensity of the light beam totally reflected at the face of the metal film, which comprises: intermittently supplying a sample liquid containing a test substance to be measured; and measuring and extracting the change in surface plasmon resonance in a state where the flow of the liquid has been stopped.

11. The measurement method of claim 10 wherein there is used a surface plasmon resonance measurement device, which comprises: a dielectric block; a metal film formed on one side of the dielectric block; a light source for generating a light beam; an optical system for allowing the above-described light beam to enter the above-described dielectric block so that total reflection conditions can be obtained at the interface between the above-described dielectric block and the above-described metal film and so that various incidence angles can be included; a flow channel system comprising a cell formed on the above-described metal film; and a light-detecting means for detecting the state of surface plasmon resonance by measuring the intensity of the light beam totally reflected at the above-described interface.

12. The measurement method of claim 10 wherein the ratio (Ve/Vs) of the amount of a sample liquid used for a single measurement (Ve ml) to the volume of the above-described cell (Vs ml) is between 1 and 100.

13. The measurement method of claim 12 wherein the ratio (Ve/Vs) is between 1 and 50.

14. The measurement method of claim 10 wherein the time required for the supply of the liquid when the sample liquid is intermittently supplied is between 0.01 second and 10 seconds per a single operation.

15. The measurement method of claim 10 wherein the time required for the stop of the liquid flow when the sample liquid is intermittently supplied is between 1 second and 20 seconds per a single operation.

16. A method for detecting or measuring a substance interacting with a physiologically active substance, which uses at least a cell, onto the surface of which a physiologically active substance binds via a covalent bond, and which comprises a step of measuring the change in surface plasmon resonance by the method of claim 10 to determine the presence of the substance interacting with the physiologically active substance.

17. The measurement method of claim 10 for measuring the change in surface plasmon resonance by exchanging the liquid in a flow channel system with another liquid, wherein a sample liquid containing a test substance to be measured is intermittently supplied when a reference liquid containing no test substances to be measured, contained in the above flow channel system, is exchanged with the above sample liquid containing a test substance to be measured, and the change in surface plasmon resonance is then measured and extracted in a state where the flow of the liquid has been stopped.

* * * * *